United States Patent
Sheena (10) Patent No.: US 10,993,793 B2
(45) Date of Patent: May 4, 2021

(54) SYSTEM AND METHOD FOR FOLLOWING AND CONDUCTING LABORATORY PROCEDURES

(71) Applicant: Haim Sheena, Beer Yakov (IL)

(72) Inventor: Haim Sheena, Beer Yakov (IL)

( * ) Notice: Subject to any disclaimer, the term of this patent is extended or adjusted under 35 U.S.C. 154(b) by 251 days.

(21) Appl. No.: 15/762,106

(22) PCT Filed: May 16, 2017

(86) PCT No.: PCT/IL2017/050542
§ 371 (c)(1),
(2) Date: Mar. 22, 2018

(87) PCT Pub. No.: WO2017/199244
PCT Pub. Date: Nov. 23, 2017

(65) Prior Publication Data
US 2018/0256304 A1    Sep. 13, 2018

Related U.S. Application Data

(60) Provisional application No. 62/337,491, filed on May 17, 2016.

(51) Int. Cl.
*A61D 19/04* (2006.01)
*A61K 35/52* (2015.01)
(Continued)

(52) U.S. Cl.
CPC .............. *A61D 19/04* (2013.01); *A61D 19/00* (2013.01); *A61K 35/52* (2013.01); *G02B 5/18* (2013.01);
(Continued)

(58) Field of Classification Search
CPC ...... G05B 19/409; A61D 19/00; A61D 19/04; G16H 10/40; G16H 40/67; G09G 2380/08;
(Continued)

(56) References Cited

U.S. PATENT DOCUMENTS 8,487,962 B2 *  7/2013  Quadling ........... A61C 13/0004
                                                      345/632
8,848,289 B2 *  9/2014  Amirparviz ........ G02B 27/0172
                                                      359/485.05

(Continued)

OTHER PUBLICATIONS

Scholl, Philipp M., Matthias Wille, and Kristof Van Laerhoven. X "Wearables in the wet lab: a laboratory system for capturing and guiding experiments." Proceedings of the 2015 ACM International Joint Conference on Pervasive and Ubiquitous Computing. ACM, 2015.

(Continued)

*Primary Examiner* — Navin Natnithithadha
*Assistant Examiner* — Sunita Reddy
(74) *Attorney, Agent, or Firm* — Alphapatent Associates, Ltd; Daniel J. Swirsky (57) ABSTRACT

There is provided a system and method for following and conducting laboratory procedures for preventing errors and fatigue of the user. The system involves input means, such as a microscope, and a camera connected to the input means, while the camera creates images of the input means. A computer is connected to the camera, and it processes the images so that augmented reality glasses which are also connected to the computer, are capable of having those images projected thereon. The computer also has laboratory protocol files installed thereon, and it projects images of the protocols onto the glasses. The projected images do not interfere with a user's natural vision.

10 Claims, 5 Drawing Sheets

(51) Int. Cl.
| | |
|---|---|
| *G02B 5/18* | (2006.01) |
| *G03B 35/02* | (2021.01) |
| *G03B 35/18* | (2021.01) |
| *G05B 19/409* | (2006.01) |
| *G06F 3/14* | (2006.01) |
| *G16H 10/40* | (2018.01) |
| *G06F 19/00* | (2018.01) |
| *G06F 17/00* | (2019.01) |
| *A61D 19/00* | (2006.01) |
| *G03B 15/14* | (2021.01) |
| *G06F 3/00* | (2006.01) |
| *G06F 3/01* | (2006.01) |
| *G06F 1/16* | (2006.01) |
| *G06F 3/03* | (2006.01) |
| *G02B 27/01* | (2006.01) |
| *G02B 21/36* | (2006.01) |

(52) U.S. Cl.
CPC .............. *G03B 15/14* (2013.01); *G03B 35/02* (2013.01); *G03B 35/18* (2013.01); *G05B 19/409* (2013.01); *G06F 1/163* (2013.01); *G06F 3/002* (2013.01); *G06F 3/011* (2013.01); *G06F 3/0304* (2013.01); *G06F 3/14* (2013.01); *G06F 17/00* (2013.01); *G06F 19/00* (2013.01); *G16H 10/40* (2018.01); *G02B 21/368* (2013.01); *G02B 27/017* (2013.01); *G09G 2380/08* (2013.01)

(58) Field of Classification Search
CPC ...... G02B 5/18; G02B 27/017; G02B 21/368; A61K 35/52; G06F 3/0304; G06F 19/00; G06F 17/00; G06F 3/002; G06F 3/14; G06F 1/163; G06F 3/011; G03B 15/14; G03B 35/18; G03B 35/02
USPC ...................................................... 600/33–35
See application file for complete search history.

(56) References Cited

U.S. PATENT DOCUMENTS

| | | | | |
|---|---|---|---|---|
| 9,675,319 | B1* | 6/2017 | Razzaque | A61B 6/466 |
| 2004/0254738 | A1* | 12/2004 | Zahniser | G01N 15/1475 |
| | | | | 702/19 |
| 2006/0057555 | A1* | 3/2006 | Damari | A01N 1/02 |
| | | | | 435/4 |
| 2007/0211081 | A1* | 9/2007 | Quadling | A61C 13/0004 |
| | | | | 345/632 |
| 2008/0044849 | A1* | 2/2008 | Booking | G01N 1/312 |
| | | | | 435/40.51 |
| 2008/0149832 | A1* | 6/2008 | Zorn | B82Y 35/00 |
| | | | | 250/311 |
| 2010/0046824 | A1* | 2/2010 | Dutta-Choudhury | |
| | | | | G06K 9/00134 |
| | | | | 382/133 |
| 2011/0250690 | A1* | 10/2011 | Craig | A01N 1/02 |
| | | | | 435/404 |
| 2012/0194419 | A1* | 8/2012 | Osterhout | G02B 27/0093 |
| | | | | 345/156 |
| 2013/0242392 | A1* | 9/2013 | Amirparviz | G02B 27/0172 |
| | | | | 359/485.05 |
| 2014/0070957 | A1* | 3/2014 | Longinotti-Buitoni | |
| | | | | A61B 5/6804 |
| | | | | 340/870.01 |
| 2014/0314300 | A1* | 10/2014 | Kaufman | G06K 9/00127 |
| | | | | 382/133 |
| 2014/0348363 | A1* | 11/2014 | Edwards | H04R 25/604 |
| | | | | 381/326 |
| 2015/0088546 | A1* | 3/2015 | Balram | G16H 40/63 |
| | | | | 705/3 |
| 2015/0209113 | A1* | 7/2015 | Burkholz | A61B 5/150786 |
| | | | | 600/411 |
| 2015/0209114 | A1* | 7/2015 | Burkholz | G06F 19/3418 |
| | | | | 600/562 |
| 2015/0209510 | A1* | 7/2015 | Burkholz | G06F 19/3418 |
| | | | | 604/506 |
| 2016/0054569 | A1* | 2/2016 | Lewis | G02B 27/0093 |
| | | | | 351/209 |
| 2016/0097026 | A1* | 4/2016 | Dorge | C12M 23/38 |
| | | | | 435/325 |
| 2016/0109713 | A1* | 4/2016 | Osterhout | G06F 3/03545 |
| | | | | 359/630 |
| 2016/0187654 | A1* | 6/2016 | Border | G02B 5/04 |
| | | | | 359/567 |
| 2016/0270656 | A1* | 9/2016 | Samec | A61B 3/0008 |
| 2016/0367358 | A1* | 12/2016 | Tran | A61L 27/3834 |
| 2017/0007351 | A1* | 1/2017 | Yu | A61B 90/50 |
| 2017/0227564 | A1* | 8/2017 | Muschler | G01B 11/0608 |

OTHER PUBLICATIONS

Hu, Grace, Lily Chen, Johanna Okerlund, and Orit Shaer. "Exploring the A use of google glass in wet laboratories." In Proceedings of the 33rd Annual ACM Conference Extended Abstracts on Human Factors in Computing Systems, pp. 2103-2108. ACM, 2015.

* cited by examiner

SYSTEM AND METHOD FOR FOLLOWING AND CONDUCTING LABORATORY PROCEDURES

TECHNICAL FIELD

The present invention relates to the field of laboratory machinery. More particularly, the invention relates to laboratories for In Vitro Fertilization (IVF).

BACKGROUND OF THE INVENTION

In Vitro Fertilization (IVF)
IVF is a process by which an egg is fertilized by sperm outside the body. The process involves monitoring and stimulating a woman's ovulatory process, removing an ovum or ova (egg or eggs) from the woman's ovaries and letting sperm fertilize them in a liquid in a laboratory. The fertilized egg (zygote) is cultured for 2-6 days in a growth medium and is then transferred to the same or another woman's uterus, with the intention of establishing a successful pregnancy. The lab processes for achieving a successful IVF demand strict discipline, experience and knowledge. Procedures such as Ovum Pick Up (OPU) which require high-skills and vast knowledge are done by doctors and embryologists only. Typically, a stereo microscope is used for IVF laboratory procedures. Looking through the eyepiece of the microscope for long periods, as one does when performing IVF, is very tiring. The solution is to have the microscope connected to a screen, so that the lab worker can look at the screen instead of the eyepiece. This solution is not perfect, since the workers still find the need to use the eyepiece.

Another challenge that an IVF lab worker faces, is the many regulations and procedures that the work entails. For instance, it is very crucial that the correct specimens of egg and sperm are taken for a single IVF procedure, and that they are not mixed-up with other specimens. There are many steps and regulations that need to be met in order to ensure that the worker does not become confused. In spite of the many regulations, the "human error" factor still exists. There is a need to provide a method for further preventing human error.

Augmented Reality (Wikipedia)
Augmented reality (AR) is a live direct or indirect view of a physical, real-world environment whose elements are augmented (or supplemented) by computer-generated sensory input such as sound, video, graphics or GPS data. It is related to a more general concept called mediated reality, in which a view of reality is modified (possibly even diminished rather than augmented) by a computer. As a result, the technology functions by enhancing one's current perception of reality. By contrast, virtual reality replaces the real world with a simulated one. Augmentation is conventionally in real time and in semantic context with environmental elements, such as sports scores on TV during a match. With the help of advanced AR technology (e.g. adding computer vision and object recognition) the information about the surrounding real world of the user becomes interactive and digitally manipulable. Information about the environment and its objects is overlaid on the real world. This information can be virtual or real, e.g. seeing other real sensed or measured information such as electromagnetic radio waves overlaid in exact alignment with where they actually are in space. Augmented reality brings out the components of the digital world into a person's perceived real world. AR displays can be rendered on devices resembling eyeglasses. Versions include eyewear that employ cameras to intercept the real world view and re-display its augmented view through the eye pieces and devices in which the AR imagery is projected through or reflected off the surfaces of the eyewear lens pieces.

SUMMARY OF THE INVENTION

Accordingly, it is a principal object of the present invention to overcome the limitations of prior art systems for conducting laboratory procedures.

Generally speaking, the present invention is directed for use of augmented reality glasses in preparation of IVF laboratory procedures.

The inventive system is intended to ease the strain of a user working on a microscope for long periods of time and preventing mistakes. It is an object of the present invention to provide a system for following and conducting laboratory procedures, said system comprising:
  input means;
  a camera connected to said input means, wherein said camera is capable of taking images of said input means;
  a computer connected to said camera and said computer is capable of processing said images;
  at least one pair of augmented reality glasses connected to said computer and are capable of having said images projected thereon;
    wherein said computer has laboratory protocol files installed thereon, and said computer is capable of projecting images of said protocols onto said glasses, and wherein said projected images do not interfere with a user's natural vision and
    wherein said system prevents errors and fatigue of the user.

The inventive system for following and conducting laboratory procedures of the preferred embodiment, provides convenience for the user analyzing specimens using input means such as a microscope, by using augmented reality glasses capable of having images of the specimen projected thereon so that the user is not forced to look at the specimen through an eyepiece of a microscope. Using the augmented reality glasses prevents fatigue caused by using a microscope eyepiece for long periods of time.

According to a preferred embodiment of the present invention, the augmented reality glasses are connected to a computer either by a wireless or wired connection. The computer provides a three-dimensional image of the specimen examined by the input means, and that image is then projected onto the glasses.

According to another preferred embodiment of the present invention, there is provided a computer connected to the augmented reality glasses, having laboratory protocol files installed thereon, and the computer is capable of projecting images of the protocols onto the glasses. The user can follow the steps of the protocol while simultaneously reading the protocol so that errors are prevented.

According to yet another preferred embodiment of the present invention, the projected images onto the glasses do not interfere with a user's natural vision.

According to a further preferred embodiment of the present invention, a Smartphone features applications which transmit protocols of various procedures including photos, video and audio files, to the glasses via a cable or RF transmission.

According to another further preferred embodiment of the present invention, the glasses may be adapted to reflect the visual characteristics of a user, such that if the user is near sighted or far sighted, the image presented on said glasses is adapted accordingly.

According to another preferred embodiment of the present invention, a user wearing the augmented reality glasses having wireless connection to a computer, can be situated away from the laboratory location and by so, supervise the lab workers steps.

It is an object of the present invention to provide a method for following and conducting laboratory procedures, said method comprising:

wearing augmented reality glasses and connecting them to electronic laboratory devices;

projecting a written laboratory protocol to said augmented reality glasses for a user to read so that a user can easily follow the steps of said protocol while conducting a laboratory procedure;

identifying a specimen by screening a barcode attached thereon with said augmented reality glasses;

projecting a view of the specimen to said augmented reality glasses; and micro-manipulating a specimen while viewing it through said augmented reality glasses, wherein said projections do not interfere with a user's natural vision, and wherein said method prevents fatigue of the user which is brought on by viewing a specimen through the eyepiece of a microscope.

Preferably, the input means is a stereomicroscope, and each of the objectives thereof is displayed on a different screen of the augmented reality glasses, thereby providing a three dimensional image.

Other objects and advantages of the invention will become apparent as the description proceeds.

BRIEF DESCRIPTION OF THE DRAWINGS

Preferred embodiments, features, aspects and advantages of the present invention are described herein in conjunction with the following drawings.

It should be understood that the drawings are not necessarily drawn to scale.

DETAILED DESCRIPTION OF THE EMBODIMENTS

The present invention will be understood from the following detailed description of preferred embodiments ("best mode"), which are meant to be descriptive and not limiting. For the sake of brevity, some well-known features, methods, systems, procedures, components, circuits, and so on, are not described in detail.

Figure 1:
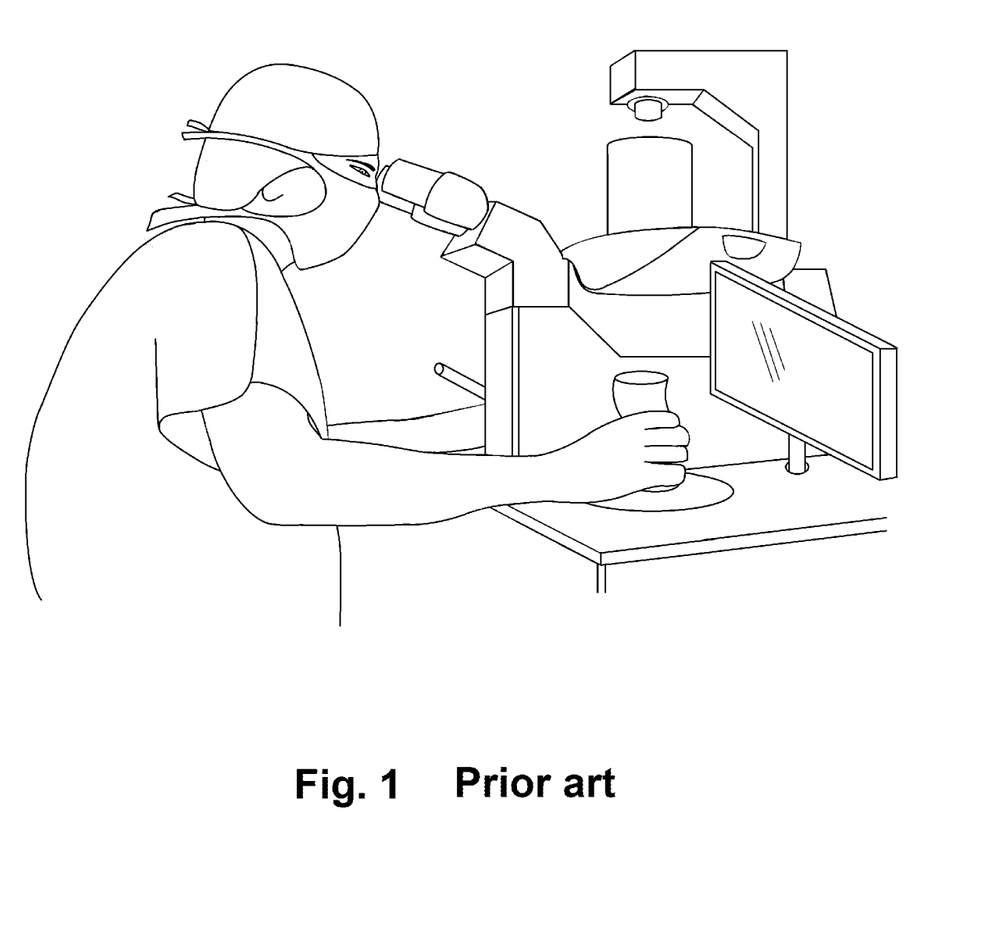
FIG. 1 shows a prior art example of a user viewing a specimen through a microscope eyepiece, also having a digital screen connected to the microscope.

In FIG. 1 there is shown a prior art example of a user viewing a specimen through a microscope eyepiece. The microscope is connected to a digital screen which shows an image of the specimen.

Figure 2:
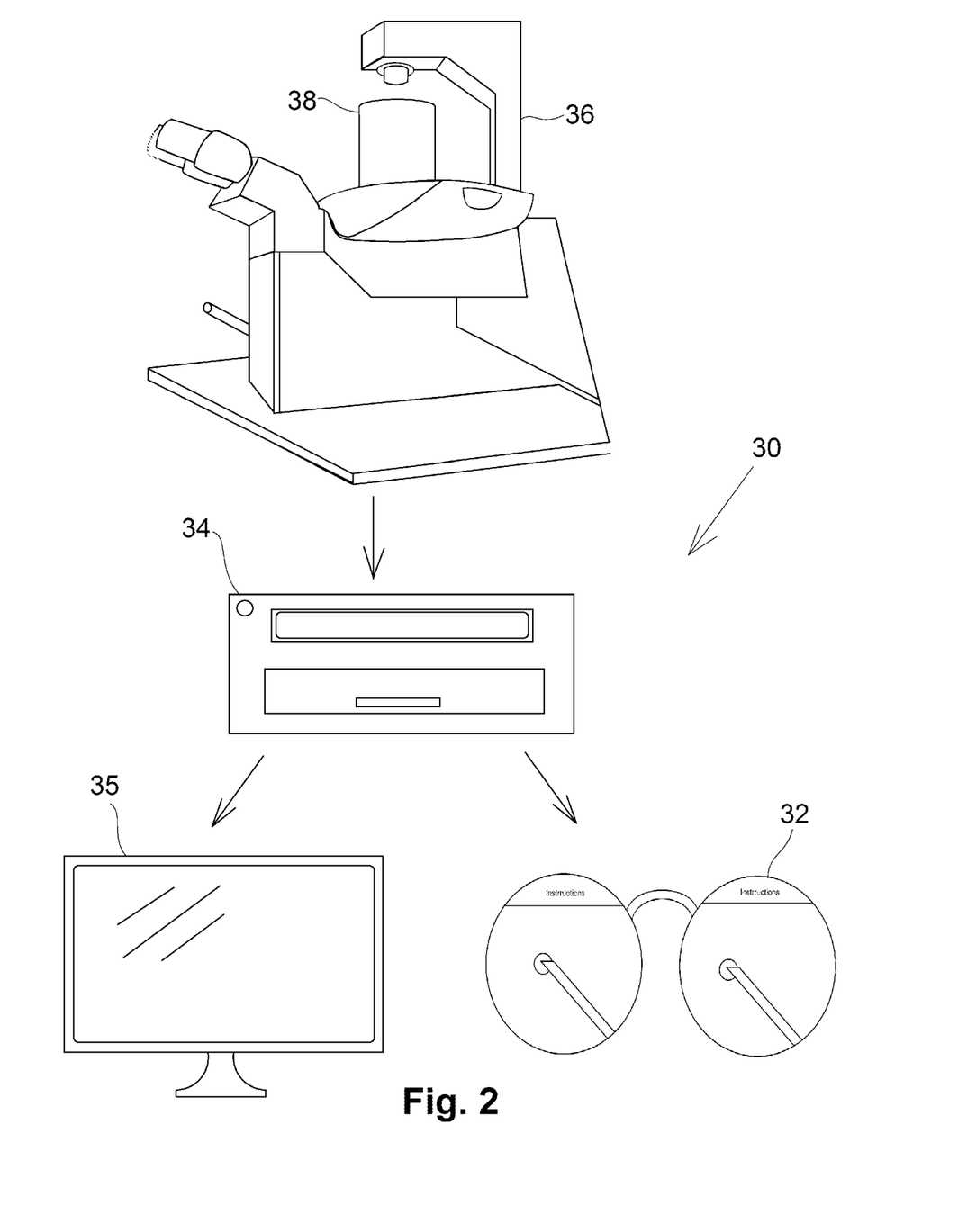
FIG. 2 shows a system for following and conducting laboratory procedures.

In FIG. 2 there is shown a system for following and conducting laboratory procedures 30. System 30 includes augmented reality glasses 32 which are connected to computer 34 via a wireless or wired connection and a microscope 36, connected to computer 34. A screen 35 may also be connected to computer 34. A video and stills camera (not shown) is connected to microscope 36. A specimen 38 is placed under microscope 36 for viewing, manipulating or treating specimen 38. The camera can photograph images, or shoot videos, of specimen 38 and project those images and movies onto glasses 32. The videos and photographed images may be saved for backup or evidence. A user (typically a lab worker or scientist) wearing glasses 32 can view specimen 38 without using an eyepiece of microscope 36, which can be very tiring after using the eyepiece for a long period of time. The glasses 32 have clear lenses so that the user has a regular view of his surroundings in addition to a view of the projected images.

In addition to having images from specimen 38 projected onto glasses 32, images of lab protocols can be projected. images of computer documents of various types, such as .pdf, .gif, .jpg etc., may be projected. The advantage of having protocols projected onto a user's glasses 32, is that the user can carefully follow the steps of the laboratory protocol while conducting the protocol, and therefore will not forget any step, and errors will be prevented.

In addition glasses 32 may be adapted to reflect the visual characteristics of a user, such that if the user is near sighted or far sighted, the image presented on glasses 32 is adapted accordingly.

Glasses 32 may have a camera installed thereon for taking photos and videos.

In another embodiment of the system 30, a Smartphone features applications which transmit protocols of various procedures including photos, video and audio files, to the glasses via a cable or RF transmission.

Figure 3:
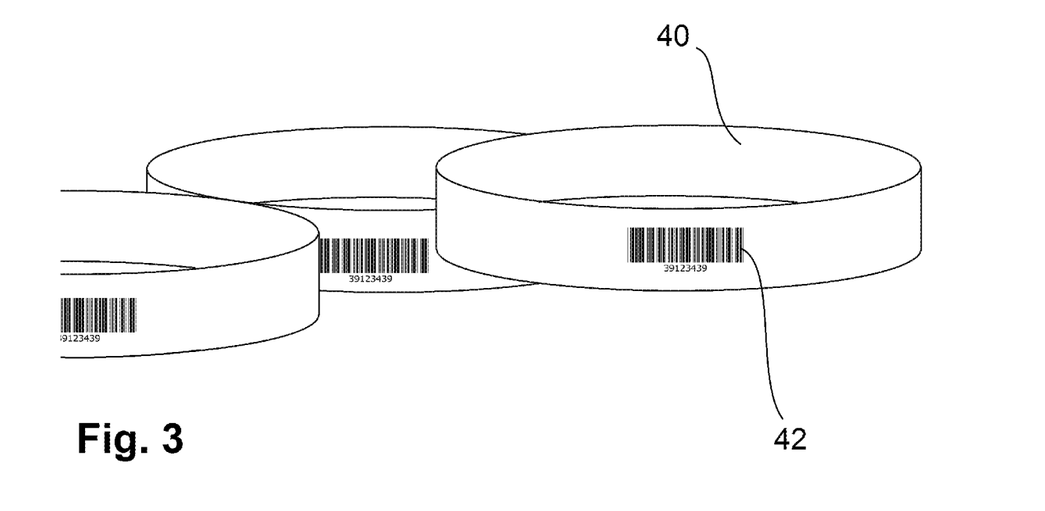
FIG. 3 shows a petri dish with a barcode.

In FIG. 3 there is shown a petri dish having a barcode 42 attached to its side, for scanning to a matching system. Barcode 42 holds information regarding the identity of the individual to whom specimen 38 (not shown here) belongs. Glasses 32 have the ability to scan a barcode 42 and read it so that the information regarding the individual will appear on glasses 32 for the user to view, and the information will be compared to a database. The matching system alerts the user if there is a mismatch by projecting a warning onto glasses 32. This feature is very important for any lab, but particularly for an IVF lab which handles both sperm specimens and egg specimens and needs to "mix" them in order for fertilization to take place. It is obviously crucial for a sperm specimen of a man to fertilize the egg specimen of his female spouse. The results of a mistake in this stage are devastating. Therefore, many precautions are to be taken to prevent such a mistake. Before working with a certain specimen, the user must scan the barcode 42, with glasses 32, on petri dish 40 so that the matching system of glasses 32 can make sure the correct specimen is being handled.

Figure 4:
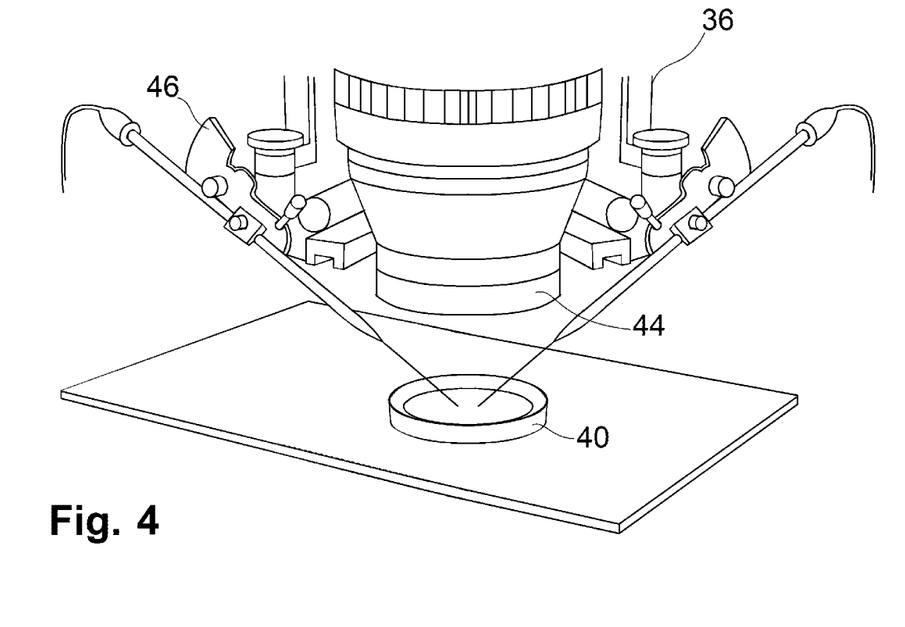
FIG. 4 shows a specimen under a microscope under the treatment of a micromanipulator.

In FIG. 4 there is shown microscope 36 having petri dish 40 placed under microscope's 36 objective 44, and a micromanipulator 46 is shown treating a specimen in petri dish 40. A camera (not shown) is connected to microscope 36 and glasses 32 (not shown here) are connected to the camera so that images taken by the camera are projected onto glasses 32, still and videos alike. The embryologist micromanipulating the specimen does not need to see it via the eyepiece of microscope 36, he can see everything on glasses 32, in real time. Using this method, IMSI (sperm morphology) can be done, as well as Intra Cytoplasmatic Sperm Injection (ICSI), laser assisted hatching or any other specific micromanipulation. For example, oocyte vitrification can be performed by projecting the oocyte vitrification protocols of different companies (such as Origio, Kitazato or Vitrolife, inclusive of preparation of the various solutions and devices). Imaging of the various stages of equilibration and vitrification can be seen. Because each step is time dependent, glasses 32 are able to notify the embryologist of the time to perform the next procedure.

In vitro culture (IVC) and embryo monitoring by time-lapse systems such as Embryoscope, Primovision, Eeva, Gavi, etc., can be connected to glasses 32, and embryo images are projected thereon.

Using glasses 32 is a very convenient method for training new employees. A simulation of the procedures can be displayed on the glasses as well.

Figure 5:
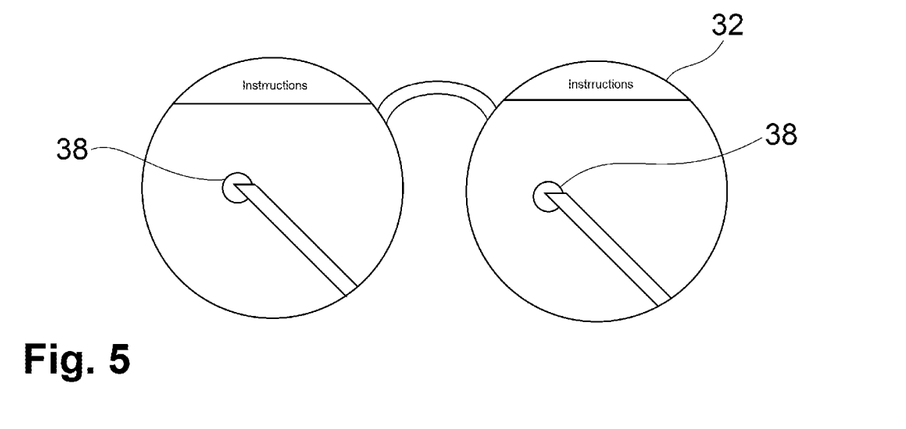
FIG. 5 shows augmented reality glasses of the present invention showing an image of a specimen being micro manipulated.

FIG. 5 shows augmented reality glasses 32 showing an image of a specimen (38) being micromanipulated. Any common IVF procedure may benefit from using glasses 32, also a procedure known as Ovum Pick Up (OPU) which is a procedure for extracting eggs from a woman's ovaries. An OPU procedure is executed by inserting a needle through the vaginal wall and into an ovarian follicle. This procedure is done under the guidance of an Ultrasound (U.S) device, and the physician needs to keep his eye on a screen showing the U.S images, during the entire procedure. By using glasses 32, there is no need to look at the screen, the U.S images are projected to glasses 32, so that the physician need not glance away from the patient to the screen. Using this method, the entire procedure is smoother, quicker and safer.

Embryo transfer (ET) into a patient's uterus can also be done using glasses 32. Ultrasound images of the endometrium will be projected onto glasses 32. Additionally, the physician performing the transfer can evaluate the embryos as seen in the stereomicroscope and will be read the details of the couple.

An additional example of a procedure that can be done using glasses 32 is sperm collection and evaluation; images of the analyzed sperm can appear on the glasses, as well as images of the sperm parameters from the microscope. Digital magnification and morphology evaluation additionally can be seen.

Figure 6:
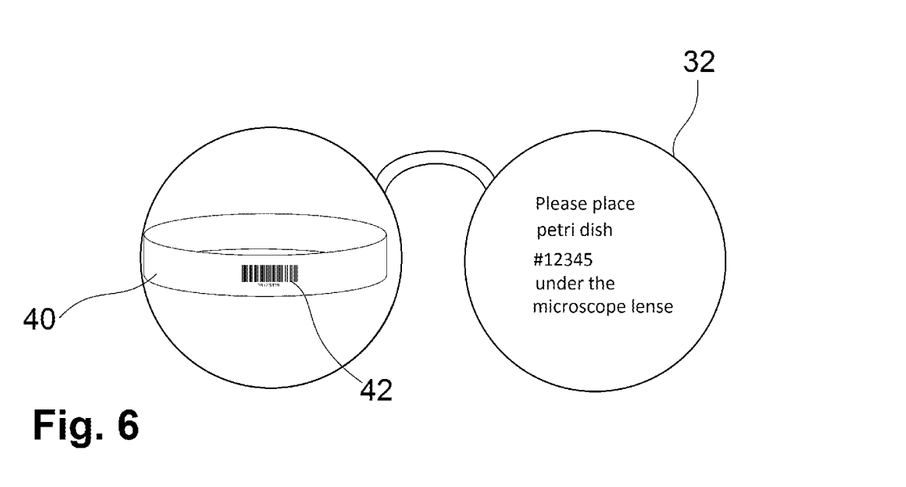
FIG. 6 shows the augmented reality glasses, showing a specimen image and a protocol image projected onto the glasses.

In FIG. 6 there is shown augmented reality glasses 32 showing a specimen image and a protocol image projected onto glasses 32. The wearer of glasses 32 can see both the image of the specimen and the written protocol of the procedure he is conducting.

Figure 7:
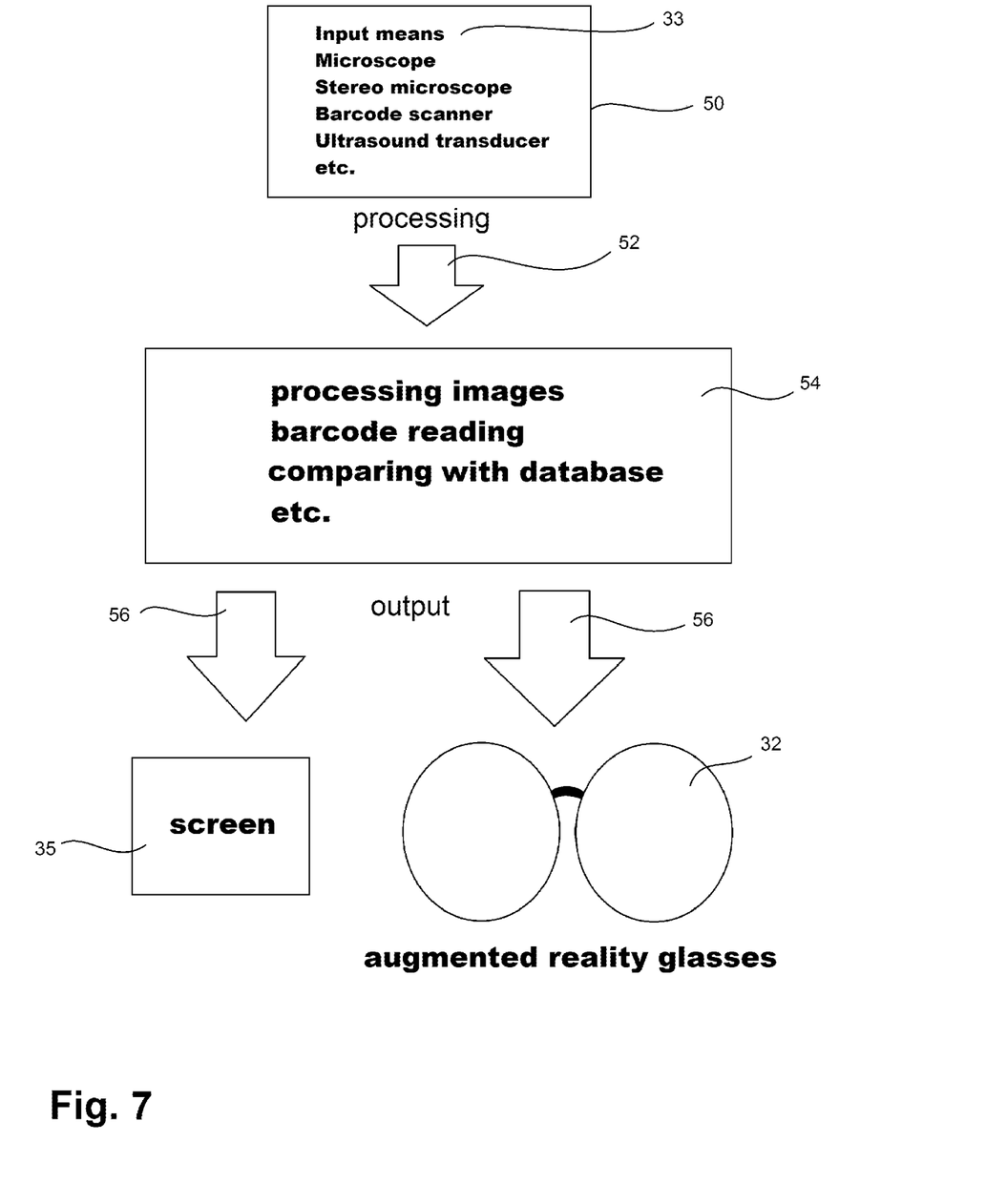
FIG. 7 shows a schematic block diagram of the system and method of the present invention.

In FIG. 7 there is shown a schematic block diagram of the architecture of the system and method of the invention. Block 50 represents the various input means that may be used for system 30, such as microscope, stereomicroscope, an inverted microscope, barcode scanner, U.S transducer, etc. Arrow 52 represents the processing of the input information of block 50, and block 54 represents the various processing operations done with the input of block 50. Arrow 56 represents the output resulting from processing operation 54, which is projected onto either/both screen 35 and augmented reality glasses 32.

In the figures and/or description herein, the following reference numerals (Reference Signs List) have been mentioned:

The system for following and conducting laboratory procedures 30
Augmented reality glasses 32
Input means 33
Computer 34
Computer screen 35
Microscope 36
Specimen 38
petri dish 40
barcode 42
Microscope objective 44
Micromanipulator 46

The foregoing description and illustrations of the embodiments of the invention has been presented for the purposes of illustration. It is not intended to be exhaustive or to limit the invention to the above description in any form.

Any term that has been defined above and used in the claims, should be interpreted according to this definition.

The reference numbers in the claims are not a part of the claims, but rather used for facilitating the reading thereof. These reference numbers should not be interpreted as limiting the claims in any form.

The invention claimed is:

1. A system for following and conducting laboratory procedures simultaneously, said system comprising:
   input means;
   a camera connected to said input means, wherein said camera is configured to accept images captured by said input means;
   a computer connected to said camera, wherein said computer is configured for processing said images; and
   at least one pair of augmented reality glasses connected to said computer for projecting said images thereon;
   laboratory protocol files installed on said computer for being projected as images by said computer onto said glasses, and
   wherein said laboratory procedures are for In Vitro Fertilization (IVF) procedures including any of ovum pickup, oocyte screening, and in vitro maturation,
   wherein said augmented reality glasses have both said images of said protocols and said input means captured images projected thereon simultaneously while concurrently visually allowing a user to view through the glasses using the user's natural vision; and
   wherein said projected images prevent errors and fatigue of the user.

2. The system of claim 1, wherein said input means is selected from a group consisting of: a microscope, a stereomicroscope, an ultrasound transducer, an inverted microscope, and a device which is connected to said camera.

3. The system of claim 1, wherein said input means connection to said camera is selected from a group consisting of: a wireless, wired connection.

4. The system of claim 3, wherein said connection is wireless and a person situated away from a laboratory location wears said glasses and by so doing, supervises a lab worker's steps.

5. The system of claim 1, wherein said computer connection to said at least one augmented reality glasses is selected from a group consisting of: wireless, wired connection.

6. The system of claim 1, further comprising a Smartphone device including an application which transmits a protocol of at least one procedure selected from a group consisting of: a photo, a video and audio files, to said glasses via a cable or radio frequency transition.

7. The system of claim 1, wherein said input means is a stereomicroscope having a plurality of objectives, wherein each of the objectives thereof is displayed on a different screen of said augmented reality glasses, thereby providing a three dimensional image.

8. A method for following and conducting laboratory procedures simultaneously, said method comprising:

wearing augmented reality glasses and connecting them to a computer;

projecting a written laboratory protocol onto said augmented reality glasses for a user to read, enabling the user to follow steps of said protocol while conducting a laboratory procedure;

connecting input means to a camera, wherein said input means examines a specimen and wherein said camera produces images of the specimen captured by said input means;

connecting said camera to said computer, wherein said computer analyzes said images produced by said camera; and projecting said images of the specimen onto said augmented reality glasses, wherein said laboratory procedures are for In Vitro Fertilization (IVF) procedures including any of ovum pickup, oocyte screening, and in vitro maturation;

wherein said augmented reality glasses have both said images of said protocol and said input means captured images projected thereon simultaneously while concurrently visually allowing the user to view through the glasses using the user's natural vision; and wherein said produced images are a video sequence and the specimen is being micromanipulated while viewing the specimen through said augmented reality glasses.

9. The method of claim 8, wherein said input means is an electrical device configured to be connected to a camera.

10. The method of claim 8, wherein said method further comprises a step of identifying the specimen situated in a petri dish by screening a barcode attached thereon with said augmented reality glasses.

* * * * *